United States Patent
Lowery et al.

(10) Patent No.: US 6,839,585 B2
(45) Date of Patent: Jan. 4, 2005

(54) PRELOADED SENSOR HOLDER

(75) Inventors: Guy Russell Lowery, San Juan Capistrano, CA (US); Asaf Danzinger, Herzliah (IL); Yoram Wasserman, Haifa (IL); Yitzhak Mendelson, Worcester, MA (US); Charles Edward Beuchat, Irvine, CA (US)

(73) Assignee: Cybro Medical, Inc., Haifa (IL)

( * ) Notice: Subject to any disclaimer, the term of this patent is extended or adjusted under 35 U.S.C. 154(b) by 2 days.

(21) Appl. No.: 10/370,119

(22) Filed: Feb. 19, 2003

(65) Prior Publication Data

US 2003/0166998 A1 Sep. 4, 2003

Related U.S. Application Data

(60) Provisional application No. 60/358,897, filed on Feb. 22, 2002.

(51) Int. Cl.[7] ............................... A61B 5/00
(52) U.S. Cl. ............................... 600/344
(58) Field of Search ................. 600/310, 323, 600/340, 344, 367, 386

(56) References Cited

U.S. PATENT DOCUMENTS 4,017,756 A * 4/1977 Davidson .......... 310/168
4,859,057 A     8/1989 Taylor et al.
5,224,478 A     7/1993 Sakai et al.
5,345,935 A     9/1994 Hirsch et al.
6,461,305 B1   10/2002 Schnall
2002/0072681 A1  6/2002 Schnali
2002/0173709 A1 11/2002 Fine et al.

OTHER PUBLICATIONS

Reflectance Pulse Oximeter At The Forehead Improves By Pressure On The Probe.

Cutting Procedure for Pro2 Adult Sensor Holder for Imagyn Medical Technologies, Nov. 26, 2002.

* cited by examiner

Primary Examiner—Eric F. Winakur
(74) Attorney, Agent, or Firm—Howard & Howard

(57) ABSTRACT

A holder for a sensor includes a body having a top wall and a side portion extending away from the top wall. The sensor is adapted to sense a parameter of an item. The top wall and the side portion of the body form an interior cavity. A flange is coupled to and extends away from an edge of the side portion. A pressure application portion is coupled to a surface of the interior cavity of the body and is adapted to apply force to the sensor when the holder is coupled to the surface of the item.

31 Claims, 4 Drawing Sheets

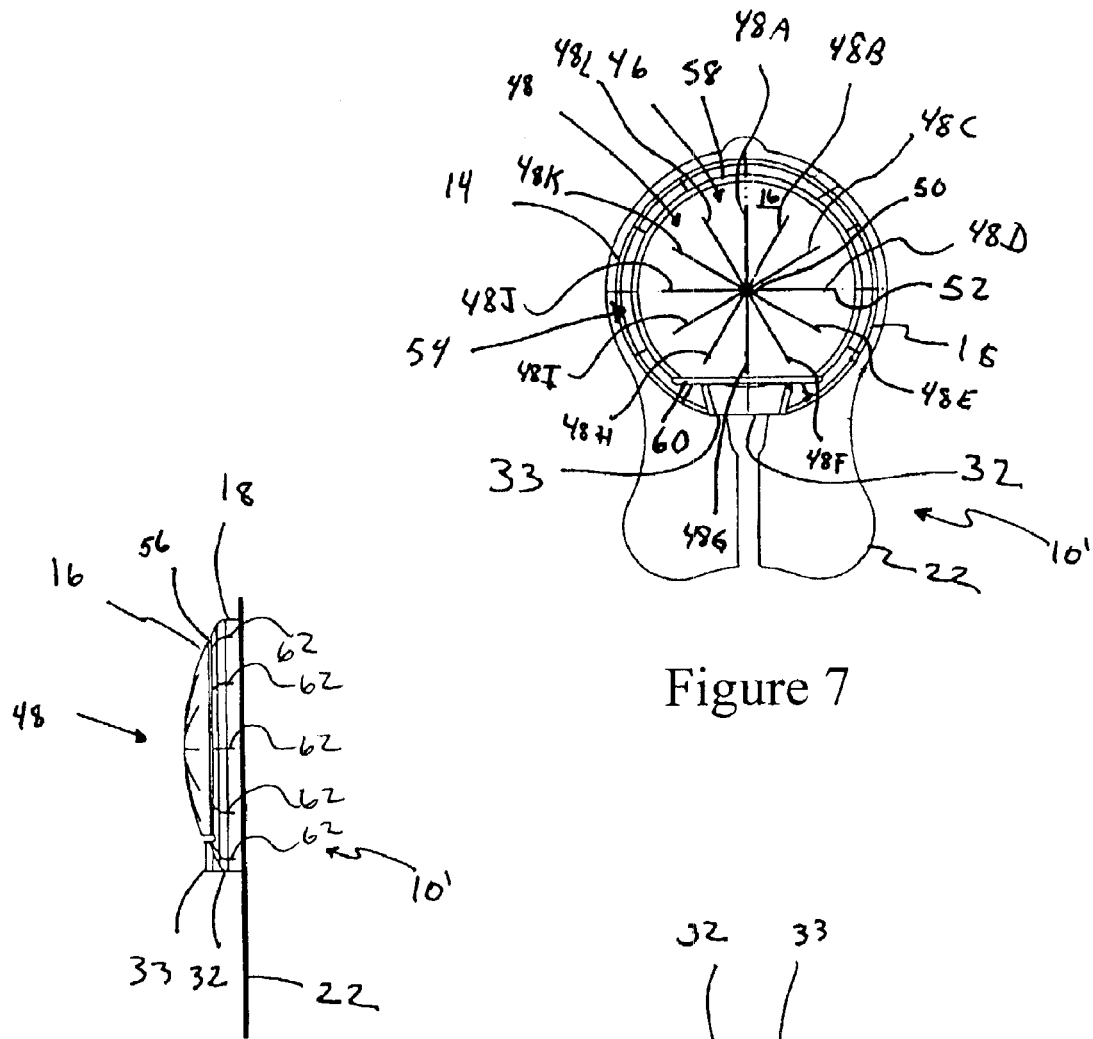
Figure 7
Figure 8
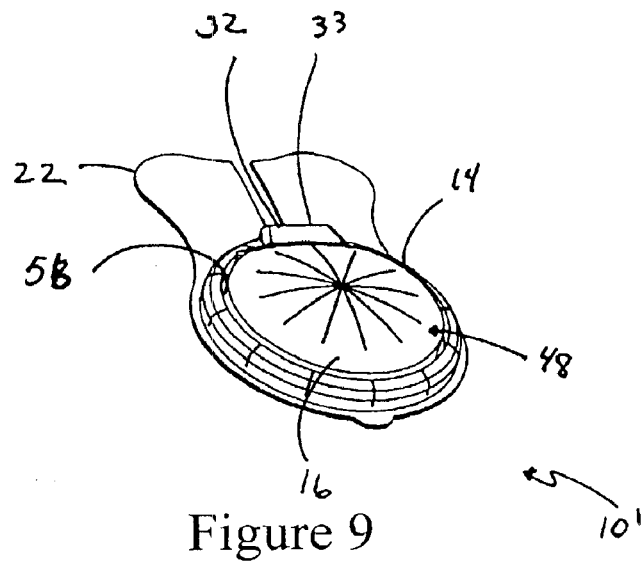
Figure 9

PRELOADED SENSOR HOLDER

The present application claims priority to U.S. Provisional Patent Application Ser. No. 60/358,897 filed Feb. 22, 2002.

FIELD OF THE INVENTION

The present invention is related generally to sensors, and more particularly, to a sensor holder which applies a predetermined force to the sensor.

BACKGROUND OF THE INVENTION

Noninvasive oximetry is based on spectrophotometric measurements of changes in the color of blood in peripheral tissues. The optical property of blood in the visible (between 500 and 700 nm) and in the near-infrared (between 700 and 1000 nm) region of the spectrum depends strongly on the amount of oxygen carried by the blood. Reduced hemoglobin, or deoxyhemoglobin (Hb), has a higher optical extinction, i.e. it absorbs more light, in the red region of the spectrum around 660 nm compared with oxygenated hemoglobin, or oxyhemoglobin ($HbO_2$). On the other hand, in the near-infrared region of the spectrum around 940 nm, the optical absorption by Hb is lower compared to $HbO_2$. The relative concentration of $HbO_2$ in arterial blood is known as $SaO_2$.

Noninvasive optical sensors for measuring arterial oxyhemoglobin saturation by a pulse oximeter (termed $SpO_2$) are comprised of a pair of small and inexpensive light emitting diodes (LEDs) and a sensitive silicon photodetector. Typically, a red (R) LED centered on a peak emission wavelength around 660 nm and an infrared (IR) LED centered on a peak emission wavelength between 880 and 940 nm are used as light sources. In transmission pulse oximetry, the sensor is usually attached across a fingertip, foot, or earlobe such that the tissue is positioned between the light source and the photodetector. In reflection or backscatter mode pulse oximetry, the LEDs and photodetector are both mounted side-by-side on the same planar substrate. This arrangement allows measurements from multiple locations on the body where transmission measurements are not feasible.

Pulse oximetry relies on the detection of photoplethysmographic signal caused by variations in the relative quantity of arterial blood volume associated with periodic contraction and relaxation of the heart. The magnitude of this signal depends on the amount of blood ejected from the heart into the peripheral vascular bed with each systolic cycle, the optical absorption of the blood, absorption by skin and tissue components, and the specific wavelengths that are used to illuminate the tissue. The value of $SpO_2$ is determined by computing the relative magnitudes of the R and IR photoplethysmograms. Electronic circuits inside the pulse oximeter separate the R and IR photoplethysmograms into their respective pulsatile (AC) and non-pulsatile (DC) signal components. An algorithm inside the pulse oximeter performs a mathematical normalization by which the time-varying AC signal at each wavelength is divided by the corresponding time-invariant DC component which results mainly from the light absorbed and scattered by the bloodless tissue, residual arterial blood when the heart is in diastole, venous blood and skin pigmentation. Since it is assumed that the AC portion results only from the pulsatile portion associated with the arterial blood component, this scaling process provides a normalized R/IR ratio which is highly dependent on $SaO_2$ and is largely independent of the volume of arterial blood entering the tissue during systole, skin pigmentation, skin thickness and vascular structure. Hence, the instrument does not need to be re-calibrated for measurements on different patients. The empirical relationship between $SaO_2$ and the normalized R/IR ratio measured by the sensor is programmed by the manufacturers into the pulse oximeter.

Noninvasive reflectance pulse oximetry has recently become an important new clinical technique with potential benefits in fetal and neonatal monitoring. The main reason for this application is the need to measure $SaO_2$ from multiple convenient locations on the body (e.g. the head, torso, or upper limbs), where conventional transmission pulse oximetry cannot be used. Using reflectance oximetry to monitor $SaO_2$ in the fetus during labor, where the only accessible location is the fetal cheek or scalp, provides additional convenient locations for sensor attachment.

While transmission and reflection pulse oximetry are based on similar spectrophotometric principles, it is widely known that reflection pulse oximetry is more challenging to perform and has unique problems. Therefore, practical solutions to problems associated with transmission pulse oximetry do not apply to problems associated with reflection pulse oximetry.

Reflection pulse oximetry can be adversely affected by strong ambient light generated for instance by light sources in the operating room or other light sources used for patient examination or phototherapeutic interventions. Commercially available reflectance sensors, such as the RS-10 sensor manufactured by Nellcor Puritan Bennett Corporation, are comprised of optical components imbedded in an optically opaque material to provide structural support and optical shielding from ambient lighting. Although some of the ambient light that is directed from the back of the probe in a predominantly perpendicular or oblique orientation is attenuated by the probe material, the highly sensitive photodetectors and high gain preamplifiers used in reflectance pulse oximetry tend to saturate even by indirect ambient light that can easily reach the photodetector by propagating through adjacent tissue structures in the vicinity of the probe. Furthermore, it is known that the relatively close proximity of the photodetector to the edge of the probe does not provide adequate protection against strong ambient lights. Therefore, the manufacture warns that using this sensor in the presence of bright lights may result in inaccurate measurements and further recommends covering the site with opaque material. Trying to provide additional protection from ambient light using for example a black cloth or optically opaque tape complicates the procedure considerably since it interferes with the monitoring procedure and also does not guarantee that the ambient light is blocked from reaching the photodetector.

Another practical problem in reflection pulse oximetry is the generally very weak pulsatile AC signals that are typically about 10 to 20 times smaller in amplitude compared to AC signals detected by transmission mode pulse oximeter sensors. Consequently, the normalized AC/DC ratios derived from the reflected R or IR photoplethysmograms that are used to compute $SpO_2$ are very small and range from about 0.001 to 0.005 depending on sensor configuration or placement. In addition, the small amplitudes add considerable noise often leading to unstable readings, false alarms and inaccurate measurements of $SpO_2$.

Most methods used to improve the accuracy of reflectance pulse oximeters aim at improving the signal-to-noise ratio by influencing the circulation underneath the sensor. For example, several investigators proposed improved sensors for application in reflectance pulse oximetry based on the application of skin heating to increase local blood perfusion [for example: Mendelson, Y. and Ochs, BD, "Noninvasive pulse oximetry utilizing skin reflectance photoplethysmography", IEEE Transactions on Biomedical Engineering, vol. 35, no. 10, pp. 798–805 (1988), Mendelson, Y., Kent, J C, Yocum, B L and Birle, M J, "Design and evaluation of a new reflectance pulse oximeter sensor", Medical Instrumentation, vol. 22, no. 4, pp. 167–173 (1988), Mendelson, Y., and McGinn, M J, "Skin reflectance pulse oximetry: in vivo measurements from the forearm and calf", Journal of Clinical Monitoring, vol. 7, pp. 7–12, (1991), Takatani S, Davies, C, Sakakibara, N. et al. "Experimental and clinical evaluation of a noninvasive reflectance pulse oximeter sensor", Journal of Clinical Monitoring, vol. 8, pp. 257–266 (1992), Konig, V, Huch R, and Huch A., "Reflectance pulse oximetry—principles and obstetric application in the Zurich system", Journal of Clinical Monitoring, vol. 14, pp. 403–412 (1998)]. However, including means for heating the skin in order to increase local blood flow has practical limitations since they could cause burns to the skin especially in neonates which have very thin and sensitive skin.

Other methods, such as exerting moderate pressure on the probe [For example: Dassel, A C M, Graaff, R., Sikkema, M., Meijer, A., Zijlstra, W G, and Aarnoudse, J G, "Reflectance pulse oximetry at the forehead improves by pressure on the probe", *J. Clinical Monitoring*, vol. 11, pp. 237–244, (1995); Dassel, A C M, Graaff, R., Meijer, A., Zijlstra, W G, and Aarnoudse, J G, "Reflectance pulse oximetry at the forehead of newborns: The influence of varying pressure on the probe", *J. Clinical Monitoring*, vol. 12, pp. 421–428, (1996)], have also been shown to be effective in increasing the pulsatile signals and thereby decreasing the R/IR variability. This was partly explained by an improved SNR due to stronger AC signals resulting from a better contact between the sensor and the skin. It was hypothesized that pressure on the sensor diminishes venous blood in the tissue underneath and, consequently, the disturbing influence of pulsating and non-pulsating venous blood is reduced considerably. Also, the relative increase in the change in vessel diameter during a pulse wave due to tissue pressure enhances absorption differences and flow velocities, resulting in an increased pulse size. Clinical measurements performed by the inventors confirmed that $SpO_2$ measurements obtained using a reflectance sensor that was gently taped to the skin using a double-sided adhesive tape tend to be about 2–6% lower compared to measurements made by a standard transmission type pulse oximeter from the finger. For example, the inventors confirmed that by exerting a moderate amount of pressure on the sensor the readings are improved considerably. Accordingly, when the sensor is pressed against the skin, the readings of the reflectance pulse oximeter are increased and quickly coincide with the readings obtained by the transmission pulse oximeter. On the contrary, when the pressure on the sensor is removed, the readings by the reflectance pulse oximeter return to their initial baseline value and continue to fluctuate.

In all of the above references, other investigators failed to disclose practical means for incorporating an inexpensive, disposable and reproducible means for shielding the sensor from ambient light and simultaneously exerting adequate pressure on the probe. Improving the quality of the detected photoplethysmographic signals in reflectance pulse oximetry will be beneficial, since inaccuracies caused by noisy and weak pulsatile signals remain one of the major unsolved sources of errors in reflectance pulse oximetry.

SUMMARY OF THE INVENTION

In a first aspect of the present invention, a holder for a sensor is provided. The sensor is adapted to sense a parameter of an item. The holder includes a body having a top wall and a side portion extending away from the top wall. The top wall and the side portion of the body form an interior cavity. A flange is coupled to and extends away from an edge of the side portion. A pressure application portion is coupled to a surface of the interior cavity of the body and is adapted to apply force to the sensor when the holder is coupled to the surface of the item.

In a second aspect of the present invention, a holder for a sensor adapted to sense a parameter of an item is provided. The holder includes a body having a top wall and a side portion extending away from the top wall. The top wall and the side portion of the body form an interior cavity. A flange is coupled to and extends away from an edge of the side portion. A pressure application portion is coupled to a surface of the interior cavity of the body for applying force to the sensor when the holder is coupled to the surface of the item. Means focuses the force applied by the body to the sensor and minimizes the force applied by the body on the flange.

In a third aspect of the present invention, a holder for a sensor adapted to sense a parameter of an item is provided. The holder includes a body having a top wall and a side portion extending away from the top wall. The top wall and the side portion of the body forming an interior cavity. A flange is coupled to and extends away from an edge of the side portion. A pressure application portion is coupled to a surface of the interior cavity of the body for applying force to the sensor when the holder is coupled to the surface of the item. A slot is located within the body.

In a fourth aspect of the present invention, a holder for a sensor adapted to sense a parameter of an item is provided. The holder includes a body having a top wall and a side portion extending away from the top wall. The top wall and the side portion of the body form an interior cavity. A flange is coupled to and extends away from an edge of the side portion. A pressure application portion is coupled to a surface of the interior cavity of the body for applying force to the sensor when the holder is coupled to the surface of the item. At least one slot is located on the outer surface of the body.

In a fifth aspect of the present invention, a holder for a sensor adapted to sense a parameter of an item is provided. The holder includes a body having a top wall and a side portion extending away from the top wall. The top wall and the side portion of the body form an interior cavity. A flange is coupled to and extends away from an edge of the side portion. A pressure application portion is coupled to a surface of the interior cavity of the body for applying force to the sensor when the holder is coupled to the surface of the item. At least one radial slots is located on the outer surface of the body.

BRIEF DESCRIPTION OF THE DRAWINGS

Other advantages of the present invention will be readily appreciated as the same becomes better understood by reference to the following detailed description when considered in connection with the accompanying drawings wherein:

FIG. 7 is a top down view of the holder of FIG. 5;

FIG. 8 is a side view of the holder of FIG. 5; and,

FIG. 9 is top isometric view of the holder of FIG. 5.

DETAILED DESCRIPTION OF THE INVENTION

Figure 1A:
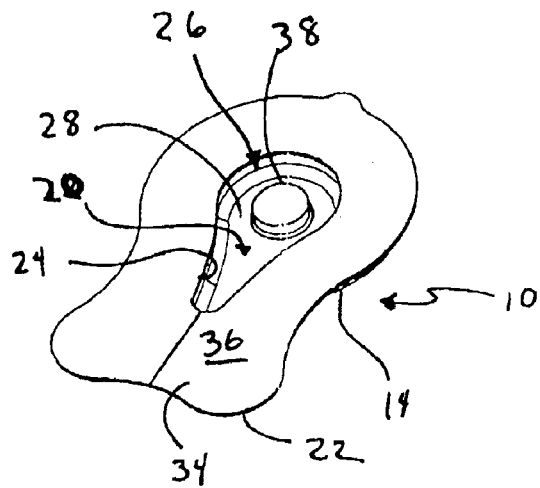
FIG. 1A is a bottom isometric view of a holder for a sensor, according to a first embodiment of the present invention.

With reference to the drawings, and in operation, the present invention provides a holder 10 for a sensor 12. The sensor 12 is being adapted to sense a parameter of an item (not shown). In one embodiment the sensor 12 is a reflectance pulse oximeter which is adapted to measure oxygen saturation in living tissue.

The holder 10 includes a body 14 having a top wall 16 and a side portion 18 extending away from the top wall 16. The top wall 16 and the side portion 18 of the body 14 form an interior cavity 20.

A flange 22 is coupled to and extends away from an edge 24 of the side portion 18. A pressure application portion 26 is coupled to a surface 28 of the interior cavity 20 of the body 14 and is adapted to apply force to the sensor 12 when the holder 10 is coupled to the surface of the item.

The body 14, flange 22, and pressure application portion 26 are integrally molded from a flexible material. In one embodiment, the body 14, pressure application portion 26, and flange 22 are integrally molded from a thermoplastic elastomer. One such material is EVOPRENE super G 946 which is available from AlphaGary Corporation of Leominster, Mass. In another embodiment, the flange 22 is made from a flexible strip or tape.

Figure 1B:
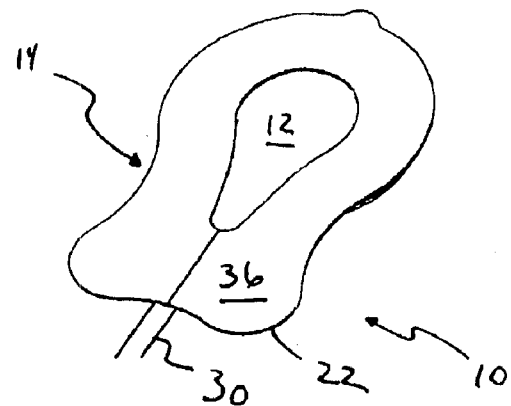
FIG. 1B is a bottom isometric view of the holder of FIG. 1 with a sensor.
Figure 2:
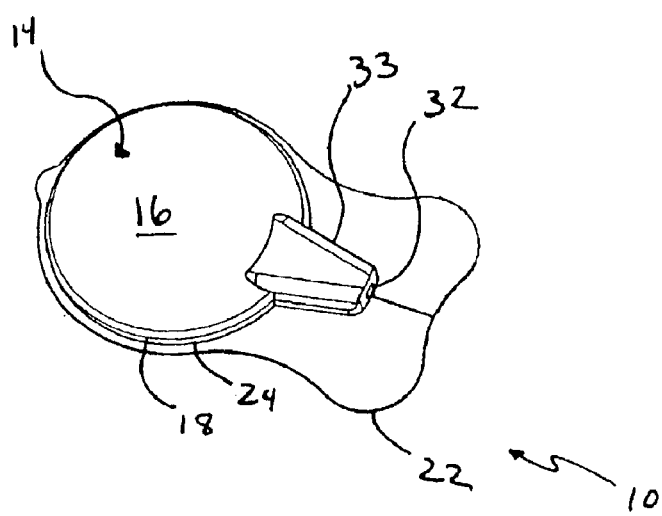
FIG. 2 is top isometric view of the holder of FIG. 1.

As shown, in FIG. 1B, the sensor 12 includes a cable 30. The body 14 includes an aperture 32 in a tail portion 33 for receiving the cable 30.

With specific reference to FIG. 1A, the holder 10 includes a layer of adhesive or adhesive tape 34 located on a surface 36 of the flange 22. The adhesive 34 is adapted for removably coupling the flange 22 to a surface of the item. The flange 22 and the adhesive 34 are adapted to shield the sensor 12 from ambient light.

In one embodiment, the pressure application portion 26 is the top wall 16 (see below). In another embodiment, the pressure application portion 26 includes a projection portion 38 extending from the top wall 16 into the interior cavity 20.

The present invention differs from the prior art in that it provides a new device to overcome the prior art limitations by providing simple and reproducible means for improving the coupling between a reflectance pulse oximeter sensor 12 and the skin; and shielding the sensitive optical components of the sensor 12 from ambient light.

Briefly described, the disposable holder 10 is made of a semi-flexible optically opaque material to prevent ambient light from reaching the sensor. The sensor 12 is inserted into the holder 10 using a minimal amount of pressure. The holder design results in easy application, removal and handling.

The advantage of utilizing this type of holder to reduce the amount of optical interference from strong ambient illumination can be clearly seen by attaching the sensor 12 to the body and comparing the signal levels measured by the sensor with and without the protective holder 10 during a constant level illumination of the sensor area by a strong light source directed toward the back of the sensor 12 as summarized in Table 1. As shown in Table 1, the relative signal intensity measured by the sensor 12 without background illumination decreased from 11,820 units without the protective holder 10 to 9,796 units when a holder 10 was used to cover the sensor 12. For comparison, with strong background illumination, the signal intensity measured by the sensor without a holder decreased from 80,477 to 11,563 when the holder was applied. These numerical values indicate that the holder 10 described is highly effective in blocking about 97.4% of the background illumination. This significant change can be attributed to the optical shielding properties provided by the holder material. Through extensive experimentation, we also discovered that similar holders with a flat surface skirt extending a minimum distance of 5 mm around the perimeter of the sensor 12 would provide adequate protection from strong ambient lighting.

TABLE 1

|  | STRONG AMBIENT ILLUMINATION [RELATIVE INTENSITY (±SD)] | NO BACKGROUND ILLUMINATION (DARK) [RELATIVE INTENSITY (±SD)] | AMBIENT/DARK RATIO [RELATIVE INTENSITY (±SD)] |
|---|---|---|---|
| SENSOR W/O HOLDER | 80,477 (±13,845) | 11,820 (±326) | 6.8 (±42.4) |
| SENSOR + HOLDER | 11,563 (±377) | 9,796 (±314) | 1.2 (±1.2) |

In addition to providing optical isolation from external light sources, the interior or molded cavity 20 matches the exact contour of the sensor body 12 and is therefore effective in limiting motion artifacts by providing a tight fit housing around the optical reflectance sensor 12 and strain relief around cable 30 that connects the sensor 12 and the pulse oximeter. The sensor holder 10 is attached to the skin by a medical adhesive material incorporated as part of the flat surface 36 of the holder 10. The pressure application portion 26 is comprised of a cushion 38. The cushion 38 in the center of the holder, which is made from the same material as the holder 10 itself, protrudes inwards and applies a uniform pressure on the sensor 12 in order to maintain a stable and intimate contact with the skin. In one embodiment, the wall thickness of the holder 10 is between 0.5 to 1.2 mm. However, the wall thickness is dependent upon the sensor 12 and the application. Thus, the present invention is not limited to any specific wall thickness. Holders with different cushion thickness could be designed to provide different amount of pressures depending on the particular medical application. From clinical experimentation, we discovered that pressures in the range between 40–130 gr/cm$^2$ provide the optimal improvement in signal intensities and pulse oximeter readings.

In one embodiment, the pressure is directly related to height of the cushion. The holder 10 has a total height 3.9 mm. In a clinical experiment, a pulse oximeter sensor having a height of 3.8 mm was tested with a holder 10 having a wall thickness of 1 mm. Clinical experimentation has shown the following relationship between cushion height and pressure (for the given holder and sensor):

| height (mm) | gr/cm2 |
|---|---|
| 0 | 40 |
| 1 | 55 |
| 2 | 70 |
| 3 | 90 |
| 4 | 110 |
| 5 | 130 |

Figure 3:
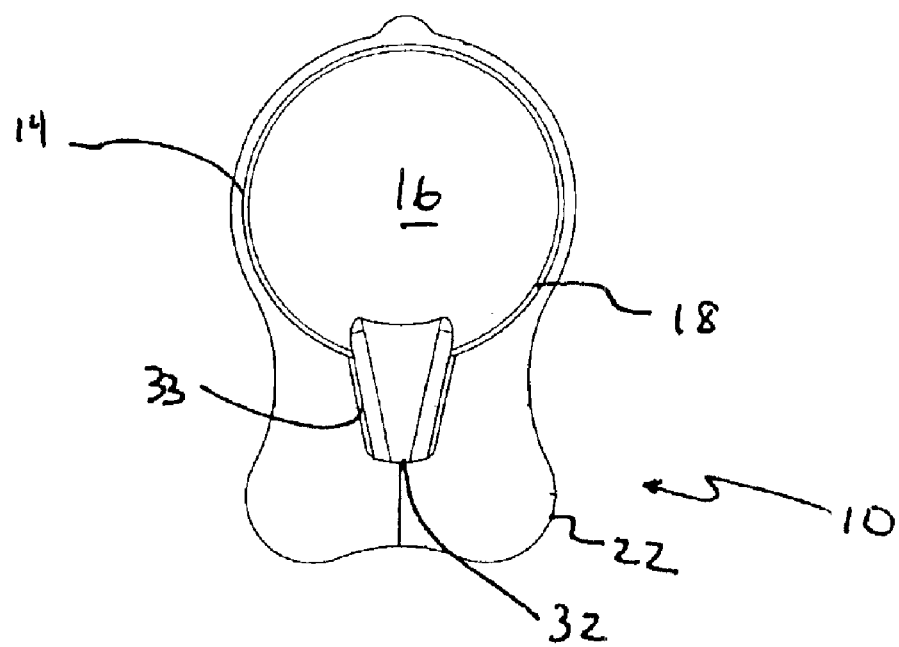
FIG. 3 is a top down view of the holder of FIG. 1.
Figure 4:
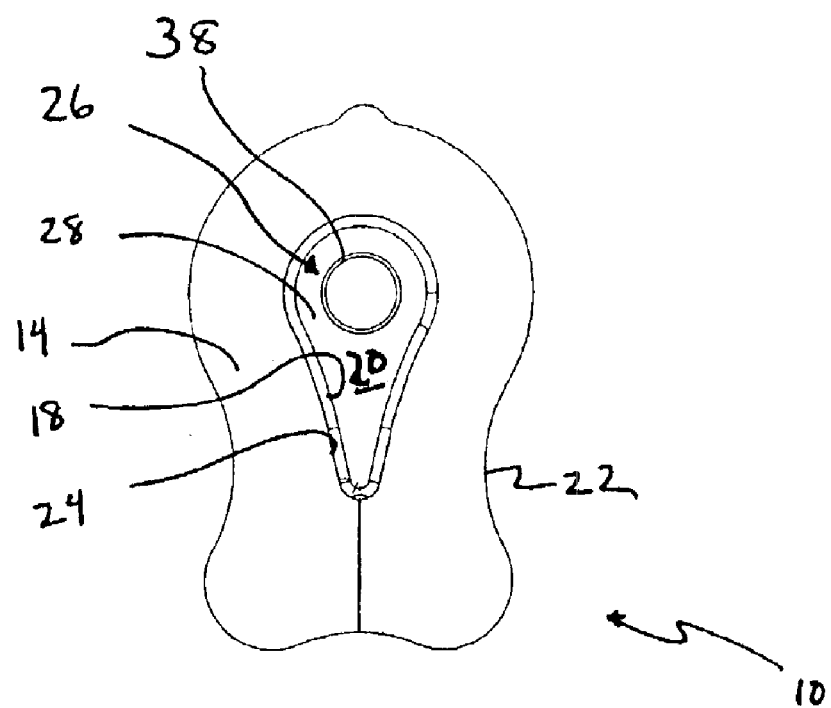
FIG. 4 is a bottom view of the holder of FIG. 1.

It should be noted that the pressure for a height of 0 mm was found through extrapolation. It should be noted that the desired pressure is dependent upon the application of the sensor, the sensor and holder dimensions, the adhesive or tape, and the material from which the holder 10 is formed. Therefore, the present invention is not limited to any specific dimensions. Other cushion wall dimensions of other embodiments of the present invention are as follows:

| Figure | Cushion Thickness (mm) | Wall Thickness (mm) |
|---|---|---|
| FIG. 3B | 1 ± 0.1 | 0.5 |
| FIG. 3C | 2.5 ± 0.25 | 0.7 |
| FIG. 3D | 3 ± 0.3 | 1.0 |
| FIG. 3E | 3.5 ± 0.35 | 1.0 |
| FIG. 3F | 5 ± 0.5 | 1.2 |

The sensor 12 is inserted into the holder 10 using a minimal amount of pressure and rests inside the holder 10.

With reference to FIGS. 5–9, wherein like parts are labeled similarly, a holder 10' for a sensor 12 adapted to sense a parameter of an item (not shown), according to a second embodiment of the present invention. The holder 10' includes means 40 means for focusing the force applied by the body 14 to the sensor 12 and minimizing the force applied by the body 14 on the flange 22. As force is applied to the sensor 12 by the pressure application portion 26, an opposite force is applied to the pressure application portion 26, and thus to the body 14, by the sensor 12. This force applied to the body 14 may be transferred to the flange 22 causing the flange 22 to become removed from the item to which it is fastened. For example, the force may cause the flange 22 to peel starting at its inner edge.

In one embodiment, the means 40 includes a focusing featuring 42 in the body 14 of the holder 10'. The focusing feature 42 distributes the load to the center of the holder 10' which allows force to be exerted on the flange 22 in the form of a pull force, as opposed to a shear or peel force.

Figure 5:
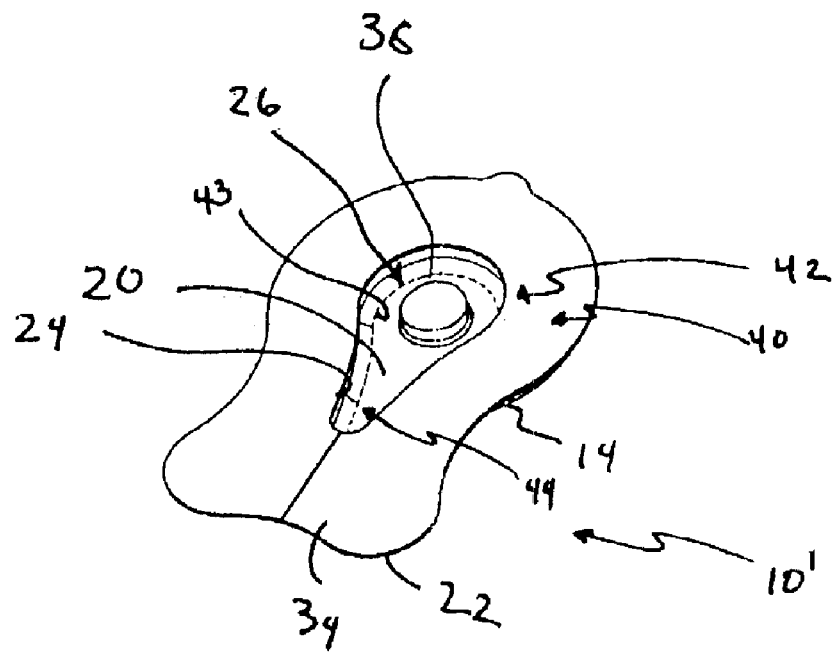
FIG. 5 is a bottom isometric view of a holder for a sensor, according to a second embodiment of the present invention.
Figure 6:
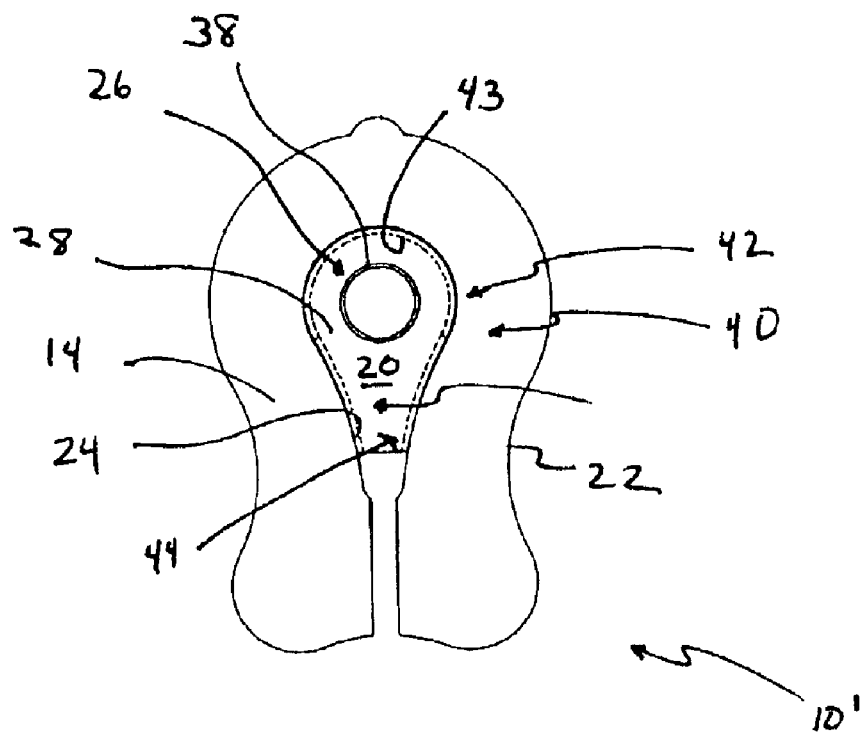
FIG. 6 is a bottom view of the holder of FIG. 5.

In a first embodiment, the focusing feature 42 is located within the interior cavity 20 of the body 14. An exemplary embodiment is shown in FIGS. 5 and 6. As shown, an interior slot 43 (in dotted lines) is formed within the body 14. The top wall 16 and the side portion 18 meet at a juncture portion 46. In the illustrated embodiment, the interior slot 43 is formed along at least a portion of the juncture portion 44. The interior slot 43 may be in the form of a cut or a groove or other suitable shape. Furthermore, the interior slot 43 may be formed during the formation of body 14, i.e., during a molding process, or after the body 14 has been formed, i.e., by a cutting or milling process.

With reference to FIGS. 7, 8 and 9 In a second embodiment, the focusing feature 42 is located on an outer surface 46 of the body.

In one aspect of the present invention, the focusing feature 42 includes at least one radial slot 48 located on the outer surface 46 of the body 14. In the illustrated embodiment, there are 12 radial slots 48A-48L located above the pressure application portion 26. As shown, the radial slots 48 have a starting point 50 located generally above the pressure application portion 26 and an ending point 52 radially spaced from the starting point 50.

In another aspect of the present invention, the focusing feature 42 includes a stiffener 54 coupled to the body 14. In one embodiment, the stiffener 54 is located within a stiffener slot 56 in the outer surface 46 of the body 14. In the illustrated embodiment, the stiffener 54 includes a first portion 58 and a second portion 60. The second portion 60 is generally linear and is located adjacent tail portion 33. The first portion 58 is located adjacent at least a portion of the outer perimeter of the body 14.

One or more transverse slots 62 may be formed in the body 14. The transverse slots 62 are adjacent the stiffener slot 56 and extend away therefrom. As with the interior slot 43, the radial slots 48, the stiffener slot 56, and/or the transverse slots 62 may be in the form of a cut or a groove or other suitable shape. Furthermore, the slots 48, 56, 62 may be formed during the formation of body 14, i.e., during a molding process, or after the body 14 has been formed, i.e., by a cutting or milling process.

Obviously, many modifications and variations of the present invention are possible in light of the above teachings. The invention may be practiced otherwise than as specifically described within the scope of the appended claims.

What is claimed is:

1. A holder for a sensor, the sensor being adapted to sense a parameter of an item, comprising:
   a body having a top wall and a side portion extending away from the top wall, the top wall and the side portion of the body forming an interior cavity, the body being flexible;
   a flange coupled to and extending away from an edge of the side portion; and,
   a pressure application portion coupled to a surface of the interior cavity of the body for applying force to the sensor when the holder is coupled to the surface of the item.

2. A holder for a sensor, as set forth in claim 1, wherein the sensor includes a cable and the body includes an aperture for receiving the cable.

3. A holder for a sensor, as set forth in claim 1, wherein the pressure application portion being integral with the top wall.

4. A holder for a sensor, as set forth in claim 1, wherein the pressure application portion includes a projection portion extending from the top wall into the interior cavity.

5. A holder for a sensor, as set forth in claim 1, further comprising a focusing feature integral with the body for focusing the force applied by the body to the sensor.

6. A holder for a sensor, as set forth in claim 5, wherein the focusing feature minimizes the force applied by the body on the flange.

7. A holder for a sensor, as set forth in claim 5, wherein the focusing feature is located within the interior cavity of the body.

8. A holder for a sensor, as set forth in claim 5, wherein the focusing feature is located on an outer surface of the body.

9. A holder for a sensor, as set forth in claim 8, wherein the focusing feature includes at least one slot located on the outer surface of the body.

10. A holder for a sensor, as set forth in claim 9, wherein the top wall and the side portion meet at a juncture portion and the focusing feature includes a slot within the body along at least a portion of the juncture portion.

11. A holder for a sensor, as set forth in claim 8, wherein the focusing feature includes at least one radial slot located on the outer surface of the body.

12. A holder for a sensor, as set forth in claim 5, wherein the focusing feature includes a stiffener coupled to the body.

13. A holder for a sensor, as set forth in claim 12, wherein the stiffener is located within a slot of the body.

14. A holder for a sensor, as set forth in claim 13, wherein the outer surface of the body has an outer perimeter, the stiffener being located along at least a portion of the outer perimeter.

15. A holder for a sensor, comprising:
a body having a top wall and a side portion extending away from the top wall, the top wall and the side portion of the body forming an interior cavity:
a flange coupled to and extending away from an edge of the side portion; and,
a pressure application portion coupled to a surface of the interior cavity of the body for applying force to the sensor when the holder is coupled to the surface of the item, body, flange, and pressure application portion being integrally molded from flexible material.

16. A holder for a sensor, comprising:
a body having a top wall and a side portion extending away from the top wall, the top wall and the side portion of the body forming an interior cavity:
a flange coupled to and extending away from an edge of the side portion; and,
a pressure application portion coupled to a surface of the interior cavity of the body for applying force to the sensor when the holder is coupled to the surface of the item, the body, flange, and pressure application portion being are integrally molded from a thermoplastic elastomer.

17. A holder for a sensor, comprising:
a body having a ton wall and a side portion extending away from the top wall, the top wall and the side portion of the body forming an interior cavity;
a flange coupled to and extending away from an edge of the side portion; and,
a pressure application portion coupled to a surface of the interior cavity of the body for applying force to the sensor when the holder is coupled to the surface of the item, the body and pressure application portion being integrally molded from flexible material.

18. A holder for a sensor, comprising:
a body having a ton wall and a side portion extending away from the top wall, the top wall and the side portion of the body forming an interior cavity;
a flange coupled to and extending away from an edge of the side portion; and,
a pressure application portion coupled to a surface of the interior cavity of the body for applying force to the sensor when the holder is coupled to the surface of the item, the body and pressure application being integrally molded from a thermoplastic elastomer and the flange is a flexible strip.

19. A holder for a sensor, comprising
a body having a top wall and a side portion extending away from the top wall, the top wall and the side portion of the body forming an interior cavity;
a flange coupled to and extending away from an edge of the side portion;
a pressure application portion coupled to a surface of the interior cavity of the body for applying force to the sensor when the holder is coupled to the surface of the item; and,
an adhesive located on a surface of the flange for removably coupling the flange to a surface of the item, wherein the flange and adhesive are adapted to shield the sensor from ambient light.

20. A holder for a sensor, comprising:
a body having a top wall and a side portion extending away from the top wall, the top wall and the side portion of the body forming an interior cavity:
a flange coupled to and extending away from an edge of the side portion;
a pressure application portion coupled to a surface of the interior cavity of the body for applying force to the sensor when the holder is coupled to the surface of the item; and,
a focusing feature integral with the body for focusing the force applied by the body to the sensor, the focusing feature being located within the interior cavity and including a slot within the body.

21. A holder for a sensor, comprising:
a body having a top wall and a side portion extending away from the top wall, the top wall and the side portion of the body forming an interior cavity;
a flange coupled to and extending away from an edge of the side portion; and,
a pressure application portion coupled to a surface of the interior cavity of the body for applying force to the sensor when the holder is coupled to the surface of the item; and,
a focusing feature integral with the body for forcing the force applied by the body to the sensor the focusing feature being located within the interior cavity of the body, the top wall and the side portion meeting at a juncture portion, the focusing feature including a slot within the body along at least a portion of the juncture portion.

22. A holder for a sensor, comprising:
a body having a top wall and a side portion extending away from the top wall, the top wall and the side portion of the body forming an interior cavity;
a flange coupled to and extending away from an edge of the side portion; and,
a pressure application portion coupled to a surface of the interior cavity of the body for applying force to the sensor when the holder is coupled to the surface of the item; and,
a focusing feature integral with the body for focusing the force applied by the body to the sensor, the focusing feature being located on an outer surface of the body and including at least one radial slot is located on the outer surface of the body, above the pressure application portion.

23. A holder for a sensor, comprising;
   a body having a top wall and a side portion extending away from the top wall; the top wall and the side portion of the body forming an interior cavity;
   a flange coupled to and extending away from an edge of the side portion;
   a pressure application portion coupled to a surface of the interior cavity of the body for applying force to the sensor when the holder is coupled to the surface of the item; and,
   a focusing feature integral with the body for focusing the force applied by the body to the sensor, the focusing feature being located on an outer surface of the body and including a plurality of radial slots located on the outer surface of the body.

24. A holder for a sensor, as set forth in claim 23, wherein the radial slots having an starting point located generally above the pressure application portion and an ending point radially spaced from the starting point.

25. A holder for a sensor, comprising:
   a body having a top wall and a side portion extending away from the top wall, the top wall and the side portion of the body forming an interior cavity;
   a flange coupled to and extending away from an edge of the side portion;
   a pressure application portion coupled to a surface of the interior cavity of the body for applying force to the sensor when the holder is coupled to the surface of the item;
   a focusing feature integral with the body for focusing the force applied by the body to the sensor, the focusing feature including a stiffener coupled to the body and being located within a slot of the body; and,
   at least one transverse slot in the body.

26. A holder for a sensor, the sensor being adapted to sense a parameter of an item, comprising:
   a body having a top wall and a side portion extending away from the top wall, the top wall and the side portion of the body forming an interior cavity;
   a flange coupled to and extending away from an edge of the side portion;
   a pressure application portion coupled to a surface of the interior cavity of the body for applying force to the sensor when the holder is coupled to the surface of the item; and,
   means for focusing the force applied by the body to the sensor and minimizing the force applied by the body on the flange.

27. A holder for a sensor, the sensor being adapted to sense a parameter of an item, comprising:
   a body having a top wall and a side portion extending away from the top wall, the top wall and the side portion of the body forming an interior cavity;
   a flange coupled to and extending away from an edge of the side portion;
   a pressure application portion coupled to a surface of the interior cavity of the body for applying force to the sensor when the holder is coupled to the surface of the item; and, a slot within the body.

28. A holder for a sensor, the sensor being adapted to sense a parameter of an item, comprising:
   a body having a top wall and a side portion extending away from the top wall, the top wall and the side portion of the body forming an interior cavity, the body being flexible;
   a flange coupled to and extending away from an edge of the side portion;
   a pressure application portion coupled to a surface of the interior cavity of the body for applying force to the sensor when the holder is coupled to the surface of the item; and,
   at least one slot located on the outer surface of the body.

29. A holder for a sensor, comprising:
   a body having a top wall and a side portion extending away from the top wall, the top wall and the side portion of the body forming an interior cavity;
   a flange coupled to and extending away from an edge of the side portion;
   a pressure application portion coupled to a surface of the interior cavity of the body for applying force to the sensor when the holder is coupled to the surface of the item; and,
   at least one slot located on the outer surface of the body, above the pressure application portion.

30. A holder for a sensor, the sensor being adapted to sense a parameter of an item, comprising:
   a body having a top wall and a side portion extending away from the top wall, the top wall and the side portion of the body forming an interior cavity, the body being flexible;
   a flange coupled to and extending away from an edge of the side portion;
   a pressure application portion coupled to a surface of the interior cavity of the body for applying force to the sensor when the holder is coupled to the surface of the item; and,
   at least one radial slot located on the outer surface of the body.

31. A holder for a sensor, comprising:
   a body having a top wall and a side portion extending away from the top wall, the top wall and the side portion of the body forming an interior cavity;
   a flange coupled to and extending away from an edge of the side portion;
   a pressure application portion coupled to a surface of the interior cavity of the body for applying force to the sensor when the holder is coupled to the surface of the item; and,
   at least one radial slot located on the outer surface of the body, the at least one radial slot having a starting point located generally above the pressure application portion and an ending point radially spaced from the starting point.

* * * * *